United States Patent [19]

Kortenbach et al.

[11] Patent Number: 5,624,459
[45] Date of Patent: Apr. 29, 1997

[54] TROCAR HAVING AN IMPROVED CUTTING TIP CONFIGURATION

[75] Inventors: Juergen A. Kortenbach, Miami Springs, Fla.; Philip O. Erwin, New York, N.Y.

[73] Assignee: Symbiosis Corporation, Miami, Fla.

[21] Appl. No.: 378,741

[22] Filed: Jan. 26, 1995

[51] Int. Cl.⁶ .................................................... A61B 17/34
[52] U.S. Cl. ........................................ 606/185; 604/164
[58] Field of Search ................................. 606/167, 184, 606/185; 604/158, 164, 165, 264

[56] References Cited

U.S. PATENT DOCUMENTS

| | | |
|---|---|---|
| 4,379,458 | 4/1983 | Bauer . |
| 4,490,136 | 12/1984 | Ekbladh . |
| 4,576,589 | 3/1986 | Kraus . |
| 4,601,710 | 7/1986 | Moll . |
| 4,654,030 | 3/1987 | Moll . |
| 4,716,901 | 1/1988 | Jackson . |
| 4,810,244 | 3/1989 | Allen . |
| 4,902,280 | 2/1990 | Lander . |
| 4,931,042 | 6/1990 | Holmes . |
| 4,976,684 | 12/1990 | Broadmax, Jr. . |
| 5,009,643 | 4/1991 | Reich et al. . |
| 5,030,206 | 7/1991 | Lander . |
| 5,057,082 | 10/1991 | Burchette, Jr. . |
| 5,066,288 | 11/1991 | Deniega . |
| 5,267,964 | 12/1993 | Deniega ......................... 606/185 |
| 5,342,382 | 8/1994 | Brinkerhoff et al. . |
| 5,366,468 | 11/1994 | Fucci . |
| 5,385,572 | 1/1995 | Nobles . |

OTHER PUBLICATIONS

"New instruments for penetrating the abdominal wall. An engineering approach." by Hoskin, *Manually Invasive Therapy*, 1993 pp. 109–111.

Primary Examiner—Michael Powell Buiz
Assistant Examiner—William Lewis
Attorney, Agent, or Firm—David P. Gordon

[57] ABSTRACT

A surgical trocar has three integral single beveled blades having cutting edges which, when viewed head on, resemble a Y configuration. The distal end of each blade is formed with a leading cutting edge and a single trailing edge which define a single beveled face. The blades are arranged so that their leading edges converge to form a sharp point at the distal end of the trocar with the leading cutting edges extending proximally and radially from the point. The trocar is preferably extruded with three fins which are shifted relative to the longitudinal axis of the extrusion such that at most a first side of each fin lies along a ray from the longitudinal axis of the extrusion. Alternatively, both sides are shifted to one side of the longitudinal axis. The distal end of each fin is then ground to form a single bevel with at least a portion of the cutting edge of the beveled fin lying in a plane which includes the longitudinal axis of the extrusion and being angled proximally. The fins are preferably spaced at 120° intervals from one another about the longitudinal axis of the extrusion. The extrusion is preferably stepped proximal of the cutting edges to form a descending step for stopping the distal movement of a spring biased safety shield. The fins may be ground using the same machine used to grind a pyramidal trocar tip and will result in cutting edges with half the angle of the cutting edges of the pyramidal tip.

32 Claims, 8 Drawing Sheets

TROCAR HAVING AN IMPROVED CUTTING TIP CONFIGURATION

BACKGROUND OF THE INVENTION

1. Field of the Invention

This invention relates to surgical trocars. More particularly, this invention relates to an improved trocar having an extremely sharp tip for making incisions.

2. State of the Art

Laparoscopic surgery is widely practiced throughout the world today and its acceptance is growing rapidly. In general, laparoscopic surgery involves creating an entry port into the body of a patient by forcing a trocar carrying a trocar tube through the abdominal wall, removing the trocar and leaving the trocar tube in place. Laparoscopic tools may be inserted through the trocar tube in order to perform minimally invasive surgery or diagnostic procedures. The trocar assembly generally includes a trocar having a sharp distal tip, and a proximal housing which carries a trocar tube which surrounds the trocar and includes a sealing or valve member associated with the trocar tube. In the assembled position ready for use, the sharp tip protrudes from the distal end of the trocar tube. The trocar is inserted into the body by pressing the trocar against the patient's skin, causing the trocar tip to make an incision in the skin so that the trocar tube can penetrate the body. After penetration, the trocar is removed from the trocar tube and valve housing, leaving the valve housing exterior of the body with the trocar tube extending into the peritoneal cavity. Surgical viewing endoscopes, cameras, lenses, or other viewing instrumentation are then inserted through the trocar tube while a cutter, dissector, or other surgical instrument is inserted through another trocar tube for the purpose of manipulating and/or cutting the internal organ or tissue. It is often desirable to have several trocar tubes in place at once in order to receive several surgical instruments. In this manner, organs or tissue may be grasped with one surgical instrument, and simultaneously may be cut with another surgical instrument; all under view of the surgeon via the viewing instrumentation in place.

It is desirable for the trocar to make the smallest and least disfiguring incision possible. To this end, an extremely sharp trocar tip is preferred which requires the least amount of pushing pressure and makes a clean incision. A well known trocar tip design includes a solid cylindrical body with multiple bevels at the distal end forming a three faced pyramidal point. The pyramidal point is provided by feeding a solid aluminum or stainless steel rod through an automatic grinding machine which grinds a flat on the end of the rod at an angle of 17° to the longitudinal axis of the rod. The grinding machine rotates the rod 120° about its longitudinal axis and grinds a second 17° flat, and then rotates the rod another 120° about its longitudinal axis and grinds the third 17° flat. This known design, however, requires a relatively large force to thrust the trocar into the abdomen. In addition, the incisions made by these designs often result in excessive tearing of the skin because the beveled surfaces of the pyramidal tip tend to push the skin apart before it is cut. This is because the actual cutting edges are formed by 68° intersections of adjacent flats, whereas the optimal cutting edge for a durable knife is a 22° intersection of flats. Nevertheless, the 68° cutting edges of the three faced pyramidal tip are the sharpest possible edges for that configuration. If the grinding angle of 17° is increased or decreased, the cutting edge angle of 68° will increase according to the trigonometry of tetrahedrons.

Other trocar tip designs exist providing certain advantages over the well known pyramidal tip. U.S. Pat. No. 4,601,710 to Moll discloses a trocar assembly including a trocar having a distally biased hollow frustroconical safety shield with three radial slots. The sharp point of the trocar includes three radially arranged blades each of which has a leading cutting edge and two trailing edges forming a double beveled blade edge which is angled proximally from the tip. When the frustroconical safety shield is pressed proximally against its biasing spring, the three slots in the safety shield permit exposure of the three blades. Moll's trocar design provides a sharp cutting tip and avoids the beveled surfaces of the pyramidal tip which tend to tear and scar the skin at the entry point of the trocar. However, the three blade tip taught by Moll is expensive to make because six surfaces must be ground, and the resulting trocar is still is not as sharp as desirable.

SUMMARY OF THE INVENTION

It is therefore an object of the invention to provide a trocar which requires only a little pressure to make an incision.

It is also an object of the invention to provide a trocar having a tip which is very sharp and makes a clean incision with little or no tearing of skin.

It is a further object of the invention to provide a trocar which is inexpensive and easy to manufacture.

It is still another object of the invention to provide a trocar which can be manufactured using the same kind of grinding machine as is used to manufacture a trocar having a pyramidal tip.

In accord with the objects of the invention a trocar is provided and generally includes a tip having three integral single beveled blades having cutting edges which, when viewed head on, resemble a slightly offset Y configuration. The distal ends of each of the blades are formed with a leading (cutting) edge and a single trailing edge which define a single beveled face. The blades are arranged so that their leading edges converge to form a sharp point at the distal end of the trocar with the leading cutting edges extending proximally and radially from the point. As only one face of each blade is ground to form a single bevel, the angle of the face can be made much smaller than in a double-bevelled blade, thereby providing a very sharp cutting edge. The trocar is also easier and less expensive to manufacture.

According to one embodiment, the trocar is extruded with three fins which are shifted relative to the longitudinal axis of the extrusion such that a first side of each fin lies along a ray from the longitudinal axis of the extrusion. The distal end of each fin is then ground to form a single bevel with the cutting edge of the beveled fin lying in a plane which includes the longitudinal axis of the extrusion and being angled proximally. The fins are preferably spaced at 120° intervals from one another about the longitudinal axis of the extrusion. The extrusion is preferably turned down proximal of the cutting edges to form a descending step for stopping the distal movement of a spring biased safety shield. The trocar tip can be ground using a conventional machine which grinds the first and second fin at an angle of 17°, rotates the trocar 120°, grinds the second and third fins at an angle of 17°, rotates the trocar 120°, and grinds the third and first fins at an angle of 17°. As will be better understood from the detailed description below, the first grinding step imparts a bevel and cutting edge to the first fin and only a leading edge to the second fin. The second grinding step imparts a bevel to the second fin and a leading edge to the third fin. The third grinding step imparts a bevel to the third fin. The resulting tip has three cutting edges, each of which has a cutting edge angle of 34°, half the angle of cutting edges of a pyramidal trocar tip. By using a more sophisticated grinding machine, and in accord with a second embodiment of the invention, the cutting edge angle can be reduced even further.

According to third embodiment of the invention, the trocar is extruded with three fins which are shifted relative to the longitudinal axis of the extrusion such that both sides of each fin are shifted in the same direction away from the longitudinal axis of the extrusion. The distal end of each fin is then ground to form a single bevel with a distal portion of the cutting edge of the beveled fin lying in a plane which includes the longitudinal axis of the extrusion and a proximal portion of the cutting edge lying in a plane which is parallel to, but does not include the longitudinal axis of the extrusion.

If the angle of the cutting edge relative to the longitudinal axis of the extrusion is the same as the angle of the bevel relative to the longitudinal axis of the extrusion, a distal portion of the trocar tip will have a pyramidal point with rays approximately equal to the thickness of the fins. Additional objects and advantages of the invention will become apparent to those skilled in the art upon reference to the detailed description taken in conjunction with the provided figures.

BRIEF DESCRIPTION OF THE DRAWINGS

FIG. 2b is a broken cross sectional view taken along the line 2b—2b in FIG. 2a;

DETAILED DESCRIPTION OF THE PREFERRED EMBODIMENT

Turning now to FIGS. 1, 2, 3, and 4, the trocar 100 according to the invention includes a proximal handle 102, a central shaft 104, and a distal cutting tip 106. The distal cutting tip 106 includes three sharpened fins 106a–106c arranged in a slightly offset, substantially "Y" formation. The fins 106a–106c are spaced at approximately 120° intervals about the longitudinal axis 108 of the cutting tip 106 which is preferably collinear with the longitudinal axis of the central shaft 104. Each fin 106a–106c generally includes first and second substantially parallel side faces 110a–110c and 112a–112c, a single bevel 116a–116c, and a leading cutting edge 114a–114c defined by the intersection of the first side 110a–110c and the bevel 116a–116c.

Figure 3:
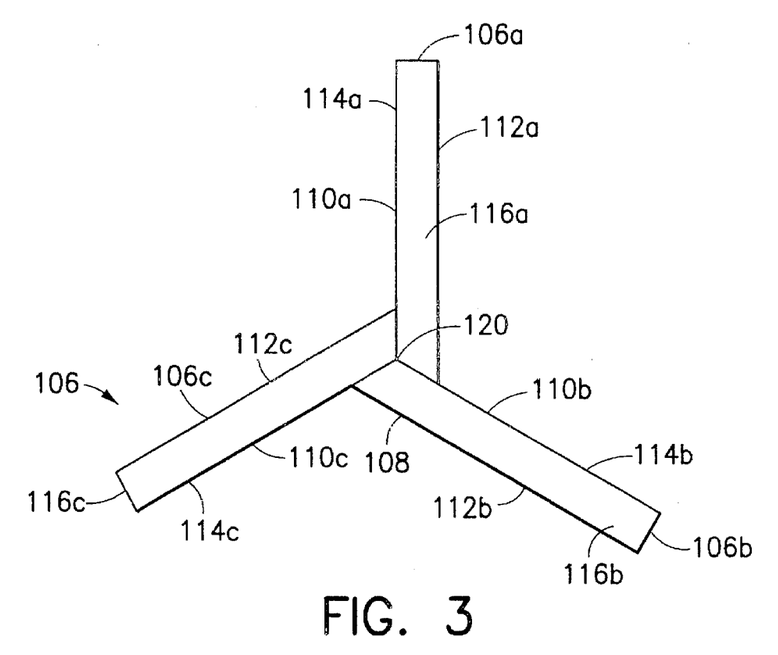
FIG. 3 is a side elevation view of the distal end of the trocar of FIG. 1.
Figure 4:
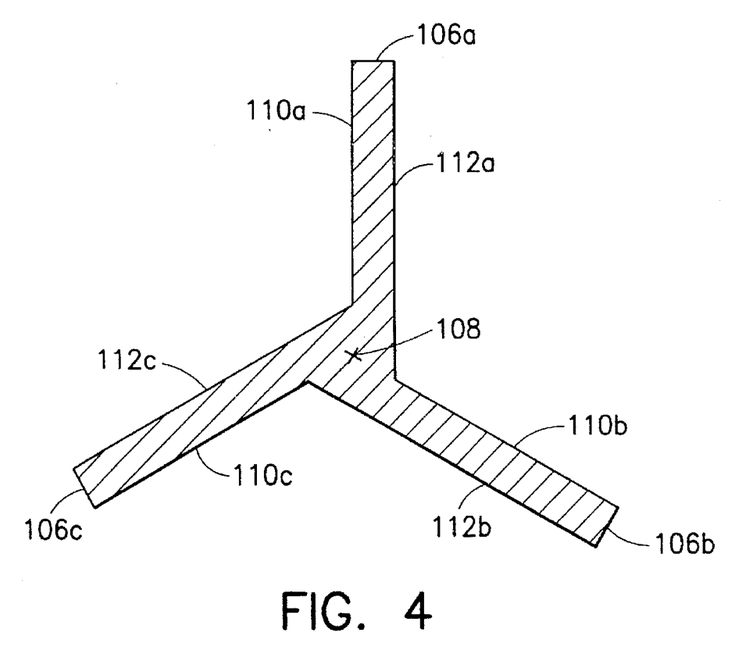
FIG. 4 is a cross sectional view along line 4—4 of FIG. 1.

As seen best in FIGS. 3 and 4, the fins are arranged so that their leading cutting edges 114a–114c extend radially outward from the longitudinal axis 108 of the cutting tip 106 and angle proximally from the distal end 120 of the cutting tip 106. As mentioned above, the leading cutting edge 114a–114c of each fin is defined by the intersection of the first side face 110a–110c with the single bevel 116a–116c. The leading cutting edge 114a–114c, and the first side face 110a–110c of each fin preferably lie in a respective first plane which includes the longitudinal axis 108 of the cutting tip 106. The second parallel side face 112a–112c of each fin therefore lies in a respective second plane which is parallel to and spaced apart from the first plane by an amount equal to the thickness of the respective fin.

According to one embodiment of the invention, the central shaft 104 and the trocar tip 106 are formed from a single integral extrusion such that the parallel sides 110a–110c and 112a–112c of the three fins are aligned with respect to the longitudinal axis 108 of the trocar 100 as described above. The distal ends of the fins 106a–106c are then ground to provide each fin with a single bevel 116a–116c as described above. Each fin is then preferably turned down to provide a step 122a–122c proximal of the cutting edge 114a–114c which continues proximally from the trocar tip 106 along the central shaft 104 to the handle 102. The steps 122a–122c are provided to accommodate a spring biased safety shield as described below.

Figure 1:
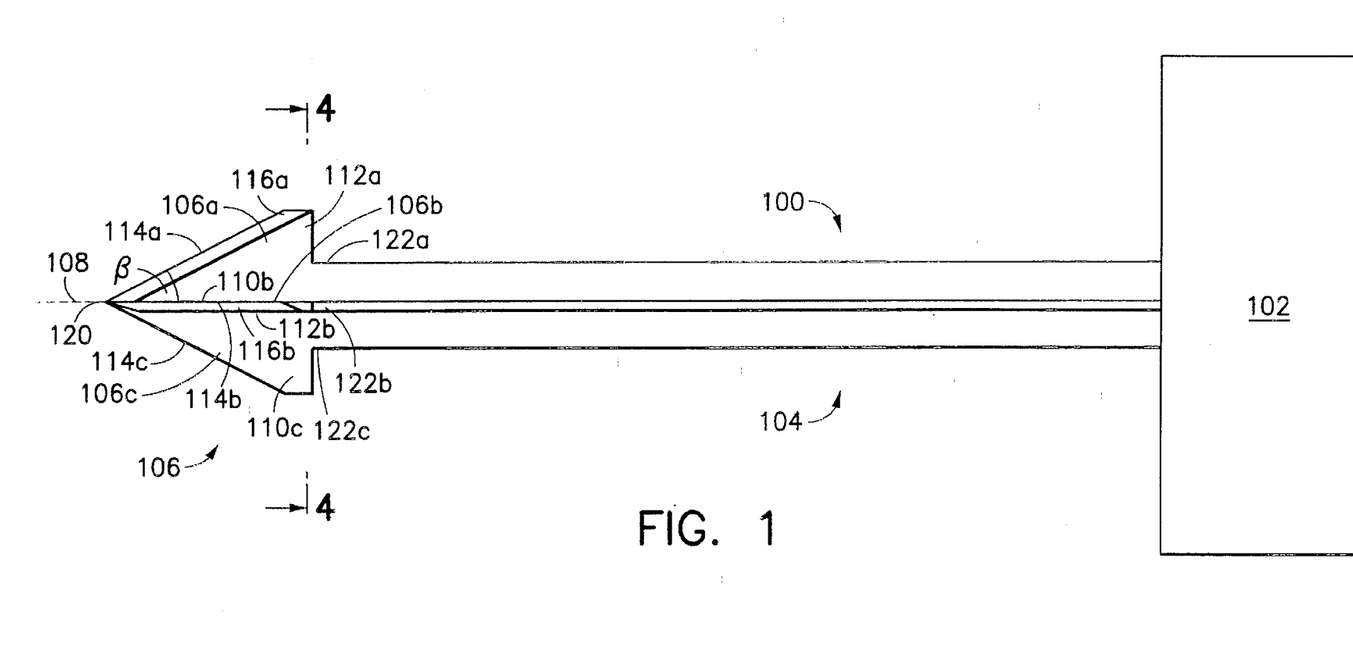
FIG. 1 is a partially schematic side elevation view of a trocar according to the invention.
Figure 2:
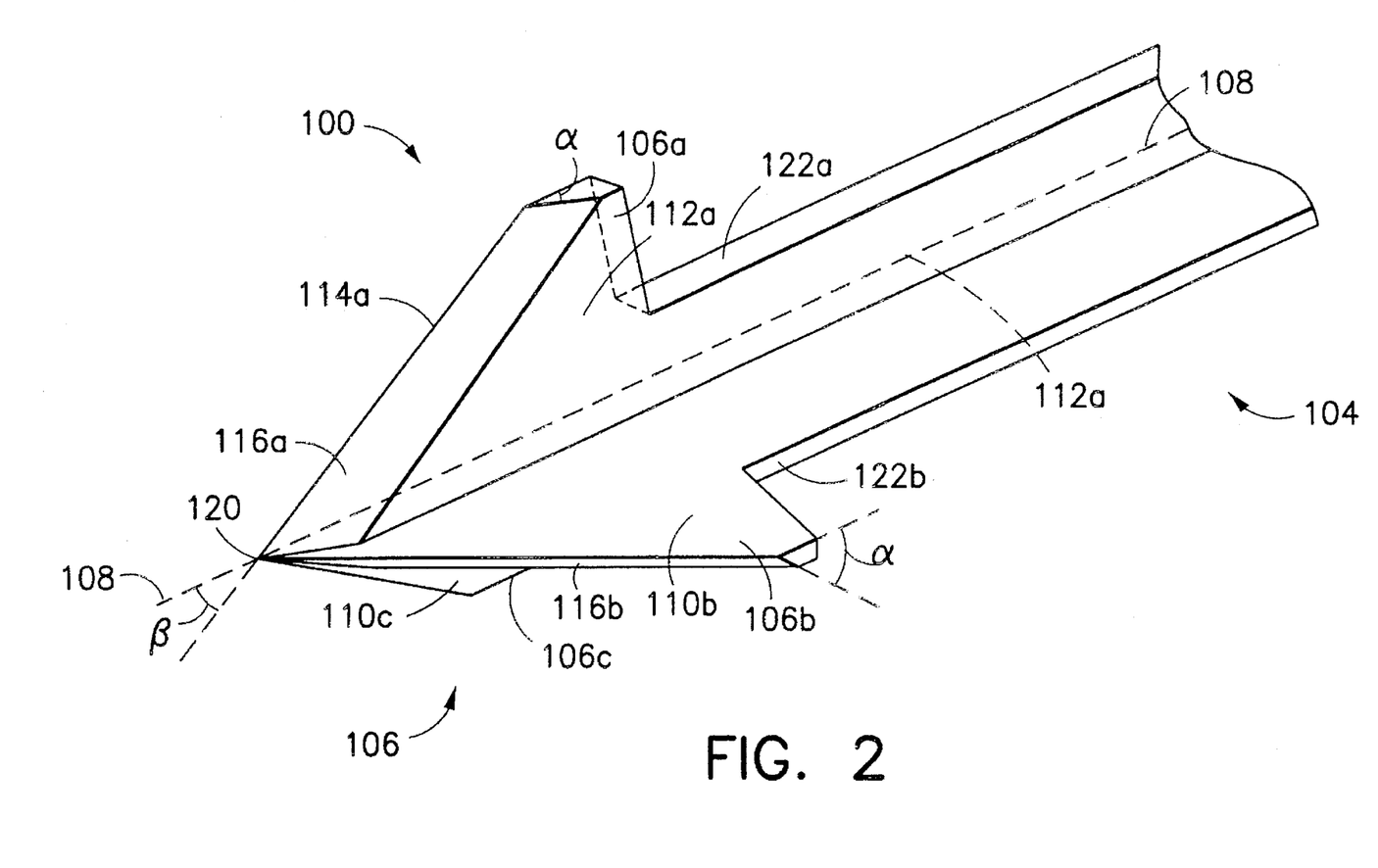
FIG. 2 is a broken perspective view of the distal end of the trocar of FIG. 1.

As seen best in FIGS. 1 and 2, each bevel 116a–116c is ground to form an acute angle α with respect to the first parallel side 110a–110c of the fin 106a–106c. Each bevel 116a–116c is also ground such that each cutting edge 114a–114c forms an acute angle β with respect to the longitudinal axis 108 of the trocar 100. The angle β is preferably approximately 17°. It will be appreciated that the Figures are drawn with exaggerated angles to better illustrate the relative features of the invention. As mentioned above, each fin 106a–106c is preferably spaced 120° apart from the other fins relative to the longitudinal axis 108 of the trocar 100.

Figure 2A:
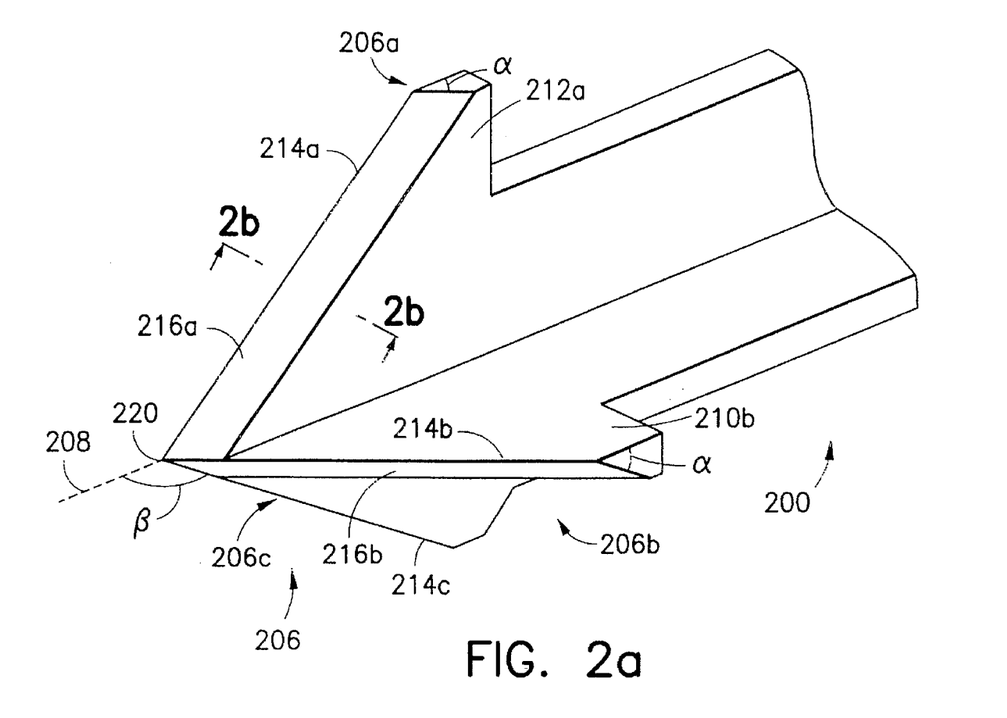
FIG. 2a is a view similar to FIG. 2 of a second embodiment of the trocar wherein the tip is machined using a conventional grinding machine.
Figure 2B:
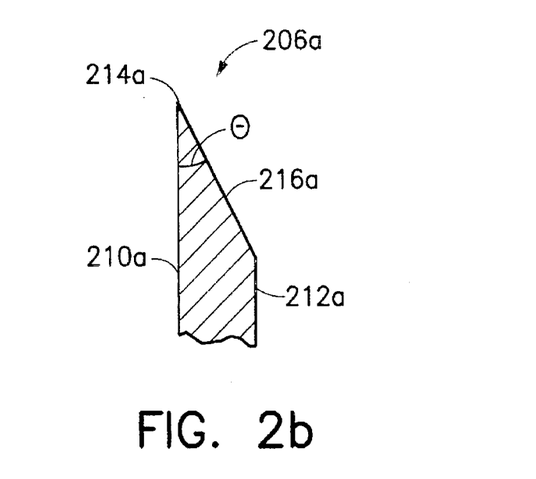

Turning now to FIGS. 2a and 2b, a trocar tip 206 is seen according to the invention where the trocar tip is ground using a conventional grinding machine such that the bevels 216a–216c are at the same angle as the cutting edges 214a–214c relative to the longitudinal axis 208; i.e., angle α equals angle β which equals 17°. In particular, the trocar tip 206 was ground using a conventional machine which ground the first and second fins 206a, 206b at an angle of 17°, rotated the trocar 120°, ground the second and third fins 206b, 206c at an angle of 17°, rotated the trocar 120°, and ground the third and first fins 206c, 206a at an angle of 17°. The first grinding step imparted a bevel and cutting edge to the first fin and only a leading edge to the second fin. The second grinding step imparted a bevel to the second fin and a leading edge to the third fin. The third grinding step imparted a bevel to the third fin. The resulting tip has three cutting edges each of which has a cutting edge angle of 34°, half the angle of cutting edges of a pyramidal trocar tip of the prior art. Comparing FIGS. 2a and 2b, it will be appreciated that the cutting edge angle φ is the angle between the first side 210 of the fin and the bevel 216 as viewed in a plane which is perpendicular to the cutting edge 214. This angle is a trigonometric function of the angles $\alpha$ and $\beta$ and equals 34° when $\alpha$ and $\beta$ are 17°. If $\alpha$ is made smaller than $\beta$, as is the case in the embodiment of FIG. 2, an even sharper cutting edge may be provided. In the embodiment of FIGS. 2a and 2b, the distal end 220 of the trocar has a pyramidal point which is defined by the intersection of the bevels 216a, 216b, 216c of one fin with the side walls 210b, 210c, 210a of a respective adjacent fin. In other words, each bevel lies in the same plane as two adjacent cutting edges. Comparing FIG. 2, above, it will be appreciated that the embodiment of FIG. 2 does not have a pyramidal tip.

Figure 5:
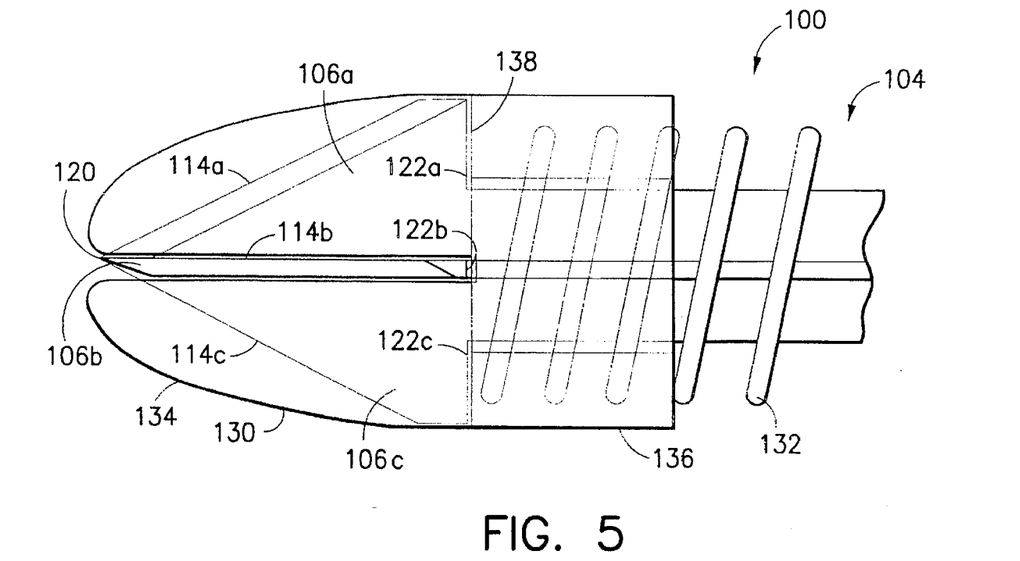
FIG. 5 is a broken transparent view of the distal end of the trocar of FIG. 1 shown with a retractable safety shield obturator in a first extended position.
Figure 6:
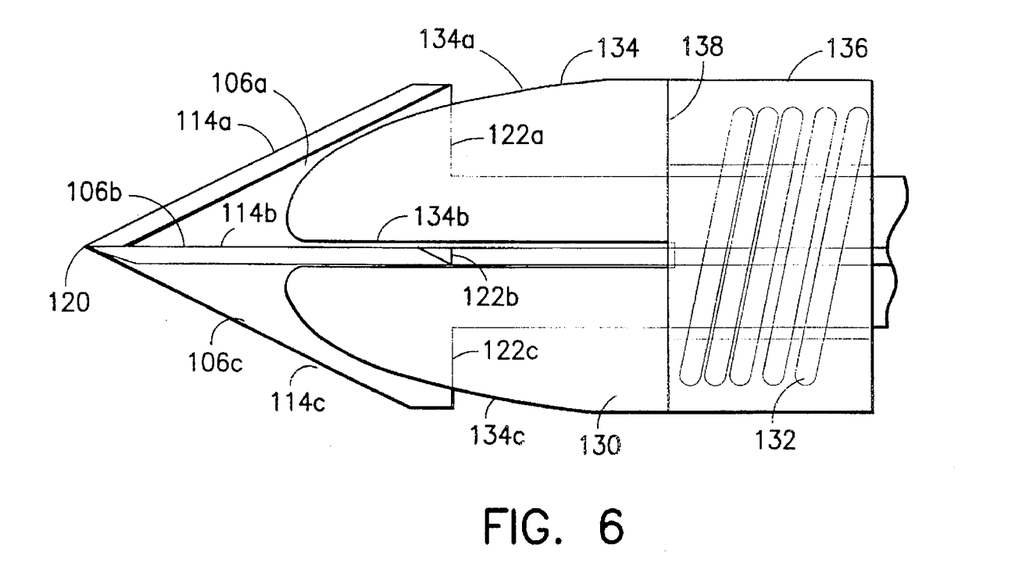
FIG. 6 is a view similar to FIG. 5 showing the safety shield in a second retracted position.
Figure 7:
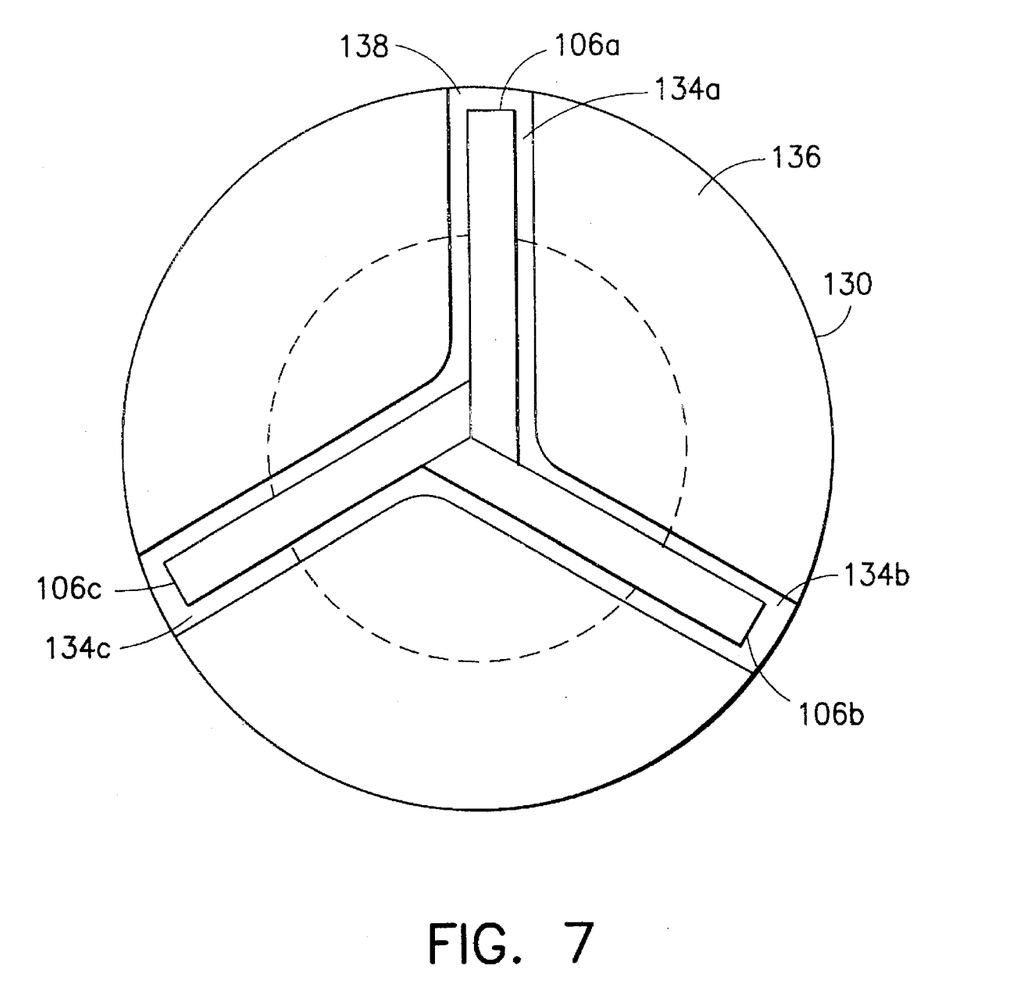
FIG. 7 is a view similar to FIG. 3, but with the safety shield of FIGS. 6 and 7.
Figure 8:
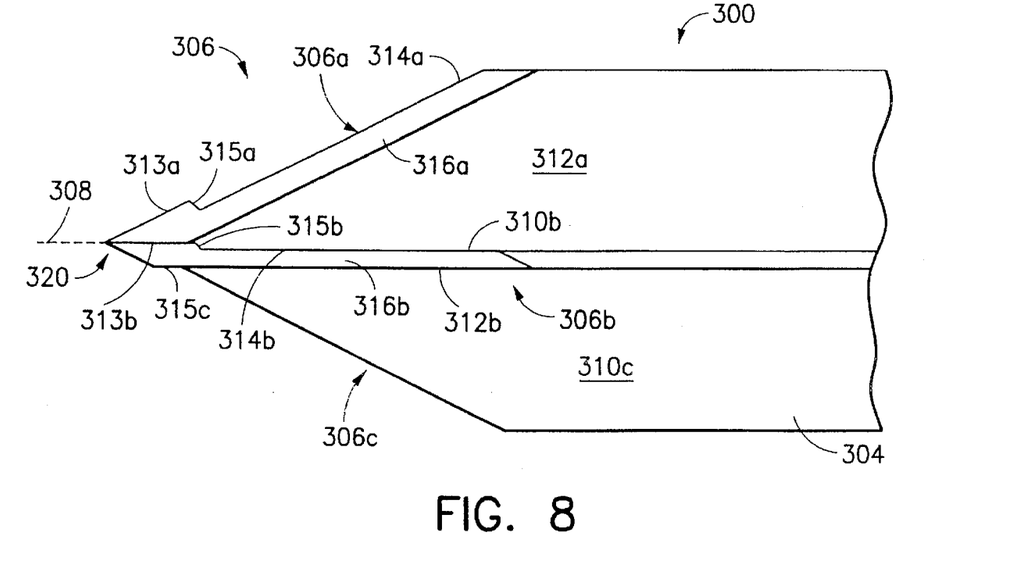
FIG. 8 is a partially schematic side elevation view of a third embodiment of the invention.
Figure 9:
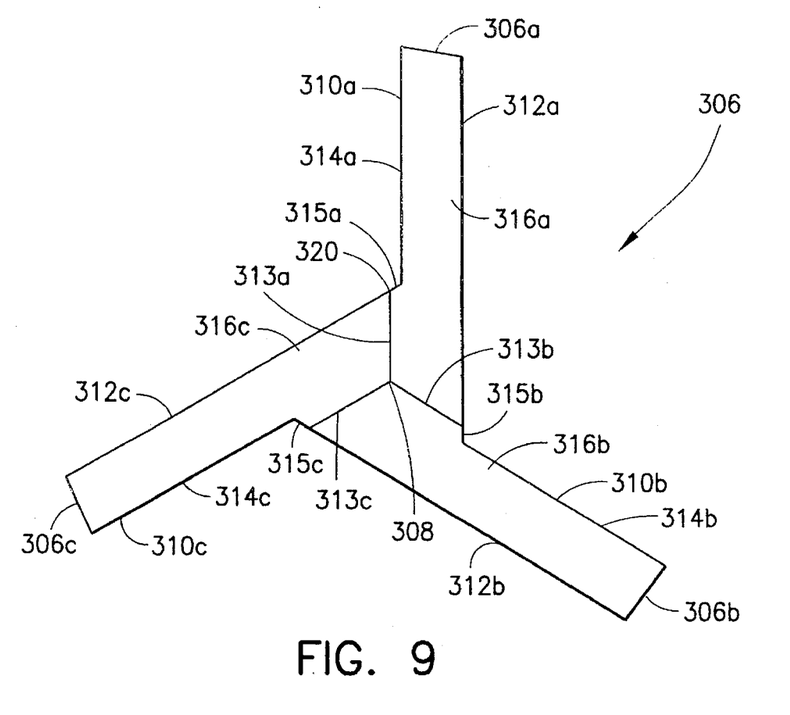
FIG. 9 is a side elevation view of the distal end of the trocar of FIG. 8.

Referring now to FIGS. 5–7, the trocar 100 (200) according to the invention is preferably provided with a safety shield 130 which is biased in the distal direction by a spring 132. The safety shield 130 is preferably a molded plastic piece having an substantially parabolical tip 134 and cylindrical base 136. The tip 134 is provided with three slots 134a–134c which are dimensioned and arranged relative to each other to receive the three fins 106a–106c of the trocar tip 106 described above. The cylindrical base 136 is provided with an annular stop 138 for receiving the spring 132. It will be appreciated that the annular stop 138 is dimensioned so that it abuts distal ends of the steps 122a–122c, i.e. the proximal ends of the fins 106a–106c when the safety shield 130 is in the first safety position as shown in FIG. 5. In this position, the tip 134 of the shield 130 extends slightly beyond the distal end 120 of the of the cutting tip 106 of the trocar 100 and the cutting edges 114a–114c are shielded by the outer surface of the tip 134 of the safety shield 130. When the safety shield is moved into the second, retracted, position, both the distal end 120 and the cutting edges 114a–114c of the cutting tip 106 are exposed. The movement of the safety shield 130 is intended to be conventional. Although not shown in the Figures, the safety shield 130 may be provided with a locking mechanism which prevents it from moving to the retracted position after it has moved once from the safety position to the retracted position and back to the safety position. The main features of the safety shield 130 according to the invention are the cooperation of the annular stop 138 with the steps 122a–122c and the arrangement of the slots 134a–134c in the tip 134 which accommodate the fins 106a–106c.

The cutting tip 106 according to the invention makes a quick and clean incision with little or no tearing of the skin and without requiring much effort on the part of the practitioner when inserting the trocar. In the preferred embodiment, the skin is incised in three directions with a substantially Y configuration (as the leading edges form a Y), thereby leaving three folded pieces of skin past which the trocar tube can enter the body.

Turning now to FIGS. 8 through 11, a third embodiment of a trocar 300 according to the invention is shown. The trocar 300 is similar to the trocars 100 and 200 described above in that it includes a proximal handle 302, a central shaft 304, and a distal cutting tip 306. The distal cutting tip 306 includes three sharpened fins 306a–306c arranged in a slightly offset, substantially "Y" formation. The fins 306a–306c are spaced at approximately 120° intervals about the longitudinal axis 308 of the cutting tip 306 which is preferably collinear with the longitudinal axis of the central shaft 304. Each fin 306a–306c generally includes first and second substantially parallel side faces 310a–310c and 312a–312c, a single bevel 316a–316c, and a leading cutting edge 314a–314c. Unlike the embodiments described above, both the first and second side faces 310a–310c and 312a–312c are both offset from the longitudinal axis 308 of the trocar 300. Because of this arrangement, which is seen best in FIG. 9, a distal portion 313a–313c of each leading cutting edge 314a–314c is not defined by the intersection of the first side 310a–310c and the bevel 316a–316c, but is defined by the intersection of adjacent bevels which intersect the longitudinal axis 308 of the trocar. In this embodiment, the distal portion 313a–313c of each cutting edge 314a–314c lies along a line which is substantially radial to the longitudinal axis 308 of the cutting tip and forms a distal pyramidal portion 320. The remainder of each cutting edge 314a–314c lies along a line which is substantially parallel to a line which is radial to the longitudinal axis 308 of the cutting tip. Thus, each cutting edge 314a–314c is provided with a slight step portion 315a–315c where the bevel 316a–316c of one fin intersects the side face 312a–312c of an adjacent fin. From the foregoing, those skilled in the art will appreciate that this embodiment of the invention offers the advantage that it is easier to grind the cutting tip to this configuration.

Figure 10:
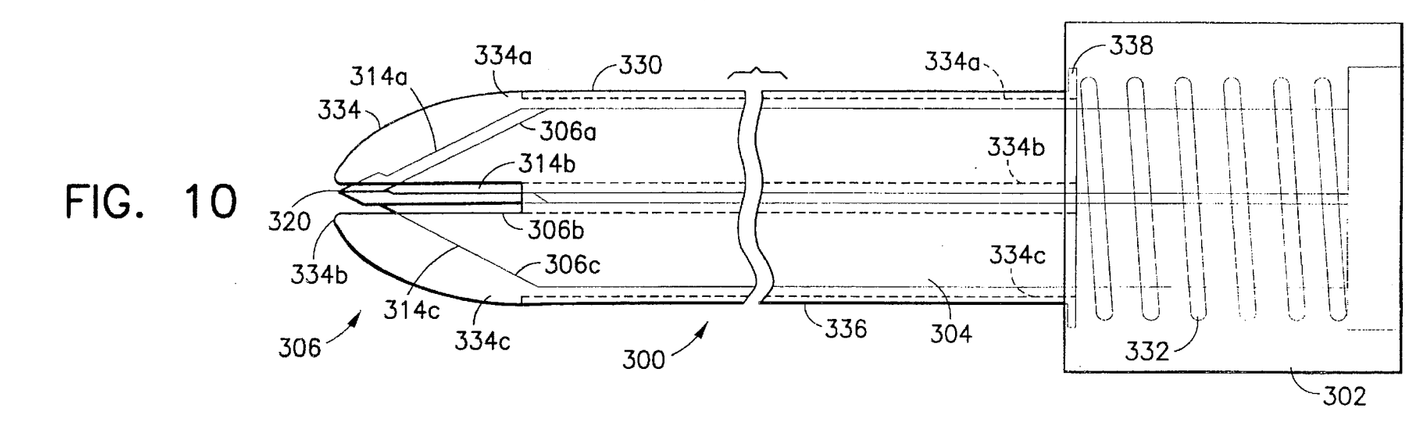
FIG. 10 is a broken transparent view of the trocar of FIG. 9 shown with a retractable safety shield obturator in a first extended position.
Figure 11:
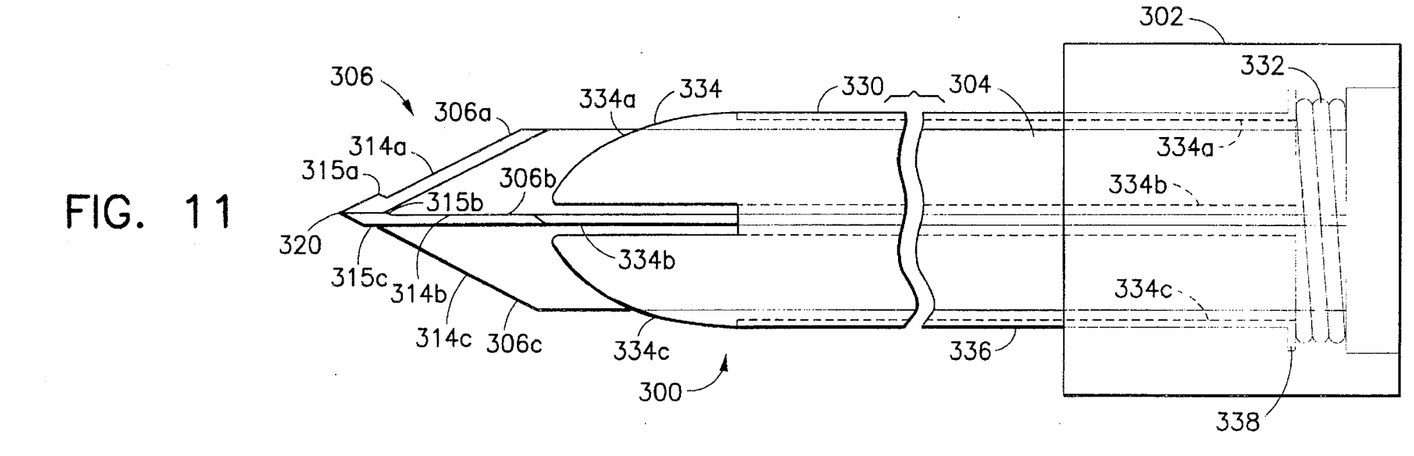
FIG. 11 is a view similar to FIG. 10 showing the safety shield in a second retracted position.

Referring now to FIGS. 10 and 11, the trocar 300 according to the invention is preferably provided with a safety shield 330 which is biased in the distal direction by a spring 332. The safety shield 330 is preferably a molded plastic piece having an substantially parabolical tip 334 and cylindrical base 336. The safety shield 330 is provided with three slots 334a–334c which are dimensioned and arranged relative to each other to receive the three fins 306a–306c of the trocar tip 306 described above. The cylindrical base 336 is provided with an annular flange 338 at its proximal end and the spring 332 biases the flange 338 in the distal direction inside the trocar handle 302. It will be appreciated that the annular flange 338 is dimensioned so that it abuts the interior of the handle 302 when the safety shield 330 is in the first safety position as shown in FIG. 10. In this position, the tip 334 of the shield 330 extends slightly beyond the distal end 320 of the of the cutting tip 306 of the trocar 300 and the cutting edges 314a–314c are shielded by the outer surface of the tip 334 of the safety shield 330. When the safety shield is moved into the second, retracted, position, shown in FIG. 11, both the distal end 320 and the cutting edges 314a–314c of the cutting tip 306 are exposed.

The movement of the safety shield 330 is intended to be conventional. Although not shown in the Figures, the safety shield 330 may be provided with a locking mechanism which prevents it from moving to the retracted position after it has moved once from the safety position to the retracted position and back to the safety position. The main features of the safety shield 330 according to the invention are the arrangement of the slots 334a–334c which accommodate the fins 306a–306c.

There have been described and illustrated herein several embodiments of a surgical trocar having an improved cutting tip configuration. While particular embodiments of the invention have been described, it is not intended that the invention be limited thereto, as it is intended that the invention be as broad in scope as the art will allow and that the specification be read likewise. Thus, while the trocar has been disclosed as having three fins and thus three cutting edges, it will be appreciated that a different number of fins could also be used. In addition, while the fins have been disclosed as being arranged at intervals of 120° relative to each other, it will be understood that other angles can be used. Also, while the grinding angle of 17°, and the cutting edge angle of 34° have been stated as preferred angles in one embodiment of the invention, it will be appreciated that other angles could be used. Moreover, while particular configurations and mechanisms have been disclosed in reference to the retractable shield, it will be appreciated that other shield mechanisms and configurations could be used as well and that the trocar could be used without a shield. Further, while the preferred embodiment disclosed herein describes an integral trocar tip and shaft, it will be appreciated that the novel trocar tip disclosed herein can be used with any type of trocar shaft and the tip and shaft need not be an integral piece. Also, while the disclosed preferred embodiment of the invention is manufactured by finishing an extruded workpiece, it will be understood that the three fins of the novel trocar tip could be made from three separate pieces and mounted in the alignment described herein. It will therefore be appreciated by those skilled in the art that yet other modifications could be made to the provided invention without deviating from its spirit and scope as so claimed.

We claim:

1. A surgical trocar comprising:
 a) a proximal handle;
 b) a distal cutting tip; and
 c) a central shaft extending from said proximal handle to said distal cutting tip, wherein
  said distal cutting tip has a longitudinal axis and a plurality of fins arranged about said longitudinal axis, each of said plurality of fins having first and second non-intersecting sides which are substantially parallel to each other and a distal bevel defining a cutting edge, said first side lying in a plane which substantially includes said longitudinal axis and said cutting edge.

2. A surgical trocar according to claim 1, wherein: said central shaft has a longitudinal axis which is collinear with said longitudinal axis of said cutting tip.

3. A surgical trocar according to claim 2, wherein: said central shaft and said distal cutting tip are an integral extruded member.

4. A surgical trocar according to claim 1, wherein: said plurality of fins is three fins.

5. A surgical trocar according to claim 4, wherein: said three fins are arranged about said longitudinal axis of said distal cutting tip at 120° intervals.

6. A surgical trocar according to claim 1, wherein: each of said cutting edges forms an acute angle with said longitudinal axis of said distal cutting tip.

7. A surgical trocar according to claim 1, wherein: said bevel forms an acute angle with said first side.

8. A surgical trocar according to claim 1, wherein: a proximal portion of each of said fins is turned down to form a step.

9. A surgical trocar according to claim 8, further comprising:
 d) a safety shield slideably mounted on said central shaft; and
 e) biasing means for biasing said safety shield in a distal direction, wherein
  said safety shield has a substantially cylindrical proximal portion and a tapered distal portion, said tapered distal portion having a plurality of slots corresponding to said plurality of fins and said substantially cylindrical proximal portion having an annular stop which prevents it from moving distally beyond said steps.

10. A surgical trocar according to claim 1, wherein: each of said cutting edges forms an angle of approximately 17° with said longitudinal axis of said distal cutting tip.

11. A surgical trocar according to claim 10, wherein: each of said bevels forms an angle of approximately 17° with said longitudinal axis of said distal cutting tip.

12. A surgical trocar according to claim 10, wherein: each of said bevels forms an angle less than approximately 17° with said longitudinal axis of said distal cutting tip.

13. In a surgical trocar having a proximal handle, a central shaft with a distal end, and a distal cutting tip having a longitudinal axis, the improvement comprising:
 said distal cutting tip comprising a plurality of fins, each fin having a first side, a second side, and a distal bevel, said first and second sides being non-intersecting and substantially parallel to each other, and said first side and said distal bevel defining a cutting edge,
 said first side and said cutting edge lying in a plane which substantially includes the longitudinal axis of said cutting tip.

14. An improved cutting tip according to claim 13, wherein: said cutting edge forms an acute angle with the longitudinal axis.

15. An improved cutting tip according to claim 13, wherein: said bevel forms an acute angle with said first side.

16. An improved cutting tip according to claim 13, wherein: said plurality of fins is three fins.

17. An improved cutting tip according to claim 16, wherein: said three fins are arranged about said longitudinal axis of said distal cutting tip at 120° intervals.

18. An improved cutting tip according to claim 13, wherein: a proximal portion of each of said fins is turned down to form a step.

19. An improved cutting tip according to claim 13, wherein: said plurality of fins are a single extruded piece.

20. An improved cutting tip according to claim 13, wherein: each of said cutting edges forms an angle of approximately 17° with said longitudinal axis of said distal cutting tip.

21. An improved cutting tip according to claim 20, wherein: each of said bevels forms an angle of approximately 17° with said longitudinal axis of said distal cutting tip.

22. A surgical trocar according to claim 20, wherein: each of said bevels forms an angle less than approximately 17° with said longitudinal axis of said distal cutting tip.

23. A surgical trocar comprising:
 a) a proximal handle;
 b) a distal cutting tip having a longitudinal axis and a plurality of fins arranged about said longitudinal axis, with each of said plurality of fins having first and second non-intersecting sides and a distal bevel defining a cutting edge; and
 c) a central shaft extending from said proximal handle to said distal cutting tip, wherein
  said first and second sides of each of said fins lie in planes which do not include said longitudinal axis, and a portion of each said cutting edge lies in a plane which substantially includes said longitudinal axis while another portion of said cutting edge lies in a plane which does not include said longitudinal axis.

24. A surgical trocar according to claim 23, wherein:
said central shaft has a longitudinal axis which is collinear with said longitudinal axis of said cutting tip.

25. A surgical trocar according to claim 24, wherein:
said central shaft and said distal cutting tip are an integral extruded member.

26. A surgical trocar according to claim 23, wherein:
said plurality of fins is three fins.

27. A surgical trocar according to claim 26, wherein:
said three fins are arranged about said longitudinal axis of said distal cutting tip at substantially 120° intervals.

28. A surgical trocar according to claim 23, wherein:
said bevel forms an acute angle with said first side.

29. A surgical trocar according to claim 23, further comprising:
d) a safety shield slideably mounted on said central shaft; and
e) biasing means for biasing said safety shield in a distal direction, wherein
said safety shield has a substantially cylindrical proximal portion and a tapered distal portion, and said tapered distal portion has a plurality of slots corresponding to said plurality of fins.

30. A surgical trocar comprising:
a) a proximal handle;
b) a distal cutting tip having a longitudinal axis and a plurality of fins arranged about said longitudinal axis; and
c) a central shaft extending from said proximal handle to said distal cutting tip, wherein
each of said plurality of fins has first and second non-intersecting sides which are substantially parallel to each other and a distal bevel defining a cutting edge having an angle substantially less than 68°.

31. A surgical trocar according to claim 30, wherein:
at least a portion of each said cutting edge forms an angle of approximately 17° with said longitudinal axis.

32. A surgical trocar according to claim 31, wherein:
said bevel forms an angle of approximately 17° with said longitudinal axis.

* * * * *